United States Patent
Cauchard et al.

(10) Patent No.: US 9,732,348 B2
(45) Date of Patent: Aug. 15, 2017

(54) APTAMERS INHIBITING THE ENZYMATIC ACTIVITY OF TYROSINASE

(71) Applicants: L V M H Recherche, Saint Jean de Braye (FR); Institut National De La Sante Et De La Recherche Medicale (Inserm), Paris (FR)

(72) Inventors: Jean Hubert Cauchard, Orleans (FR); Robin Kurfurst, Saint Jean de Braye (FR); Sylvianne Schnebert, Olivet (FR); Eric Dausse, Bordeaux (FR); Jean-Jacques Toulme, Lormont (FR)

(73) Assignees: L V M H Recherché, Saint Jean de Braye (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 14/654,950

(22) PCT Filed: Dec. 20, 2013

(86) PCT No.: PCT/EP2013/077801
§ 371 (c)(1),
(2) Date: Jun. 23, 2015

(87) PCT Pub. No.: WO2014/102213
PCT Pub. Date: Jul. 3, 2014

(65) Prior Publication Data
US 2015/0329863 A1    Nov. 19, 2015

(30) Foreign Application Priority Data
Dec. 24, 2012 (FR) ..................................... 12 62754

(51) Int. Cl.
| | |
|---|---|
| C12N 15/11 | (2006.01) |
| C12Q 1/68 | (2006.01) |
| C12N 9/74 | (2006.01) |
| C12N 15/115 | (2010.01) |
| C12N 15/10 | (2006.01) |

(52) U.S. Cl.
CPC ........ C12N 15/115 (2013.01); C12N 15/1048 (2013.01); C12Y 114/18001 (2013.01); *C12N 2310/16* (2013.01)

(58) Field of Classification Search
USPC ........................................... 536/24.5; 514/44
See application file for complete search history.

(56) References Cited

U.S. PATENT DOCUMENTS
2009/0202458 A1    8/2009 Binetti et al.

FOREIGN PATENT DOCUMENTS
| | | | |
|---|---|---|---|
| WO | WO 91/19813 | * | 6/1991 |
| WO | WO 01/58918 A1 | | 8/2001 |

OTHER PUBLICATIONS

Ando et al. (Journal of Investigative Dermatology, 2007 vol. 127, No. 4:751-761).*

(Continued)

*Primary Examiner* — Terra C Gibbs
(74) *Attorney, Agent, or Firm* — Knobbe Martens Olson & Bear LLP (57) ABSTRACT

The invention relates to a DNA aptamer that can inhibit the enzymatic activity of tyrosinase for the conversion of tyrosine into L-DOPA and dopaquinone, and to the dermatological and cosmetic uses thereof.

14 Claims, 4 Drawing Sheets

(56) References Cited

OTHER PUBLICATIONS

Jaanson et al. (European Journal of Cancer, Nov. 2012, vol. 48, Supp 6 pp. 101-102).*
Giebel et al. (Genomics, Mar. 1991;9(3):435-45).*
An, Sang Mi et al., "Inhibition of melanogenesis by tyrosinase siRNA in human melanocytes" BMB reports, Mar. 31, 2009, pp. 178-183, vol. 42, No. 3.
Ando, Hideya et al., "Approaches to Identify Inhibitors of Melanin Biosynthesis via the Quality Control of Tyrosinase" Journal of Investigative Dermatology, 2007, pp. 751-761, vol. 127.
Dupont, D.M. et al., "Nucleic Acid Aptamers Against Proteases" Current Medicinal Chemistry, 2011, pp. 4139-4151, vol. 18.
Jaanson, N. et al., "332—The Anti-tyrosinase Monoclonal Antibody is Effective in Treating Mice Bearing Syngenic Melanoma" European Journal of Cancer, Oct. 2012, pp. 101-102, vol. 48.
Lin, Shi-Lung et al., "Chapter 4—Recent Application of Intronic MicroRNA Agents in Cosmetics" Current Perspectives in Micrornas (Mirna), 2008, pp. 51-72, XP009136584.
Missailidis, S. et al., "Development of diagnostic and therapeutic aptamers against enzymes crucial for tumour development and metastasis" European Journal of Cancer, Supplement, Jun. 2010, pp. 11-12, vol. 8, No. 5.
Williams, Kelly P. et al., "PCR product with strands of unequal length" Nucleic Acids Research, 1995, pp. 4220-4221, vol. 23, No. 20.
French Search Report for 1262754 dated Oct. 2, 2013.
International Search Report for PCT/EP2013/077801 dated Feb. 21, 2014.

* cited by examiner

SEQUENCE LISTING

<160> NUMBER OF SEQ ID NOS: 19

<210> SEQ ID NO 1
<211> LENGTH: 77
<212> TYPE: DNA
<213> ORGANISM: artificial
<220> FEATURE:
<223> OTHER INFORMATION: Aptamer

<400> SEQUENCE: 1
gcctgttgtg agcctcctgt cgaacgcaat gggcgcagat tggaaggcct agcattgagc    60
gtttattctt gtctccc                                                   77

<210> SEQ ID NO 2
<211> LENGTH: 37
<212> TYPE: DNA
<213> ORGANISM: artificial
<220> FEATURE:
<223> OTHER INFORMATION: Aptamer

<400> SEQUENCE: 2
gcctcctgtc gaacgcaatg ggcgcagatt ggaaggc                              37

<210> SEQ ID NO 3
<211> LENGTH: 30
<212> TYPE: DNA

```
<213> ORGANISM: artificial
<220> FEATURE:
<223> OTHER INFORMATION: Aptamer

<400> SEQUENCE: 3
ccctgtcgaa cgcaatgggc gcagattggg                                          30

<210> SEQ ID NO 4
<211> LENGTH: 22
<212> TYPE: DNA
<213> ORGANISM: artificial
<220> FEATURE:
<223> OTHER INFORMATION: Aptamer

<400> SEQUENCE: 4
cccgaacgca atgggcgcag gg                                                  22

<210> SEQ ID NO 5
<211> LENGTH: 11
<212> TYPE: DNA
<213> ORGANISM: artificial
<220> FEATURE:
<223> OTHER INFORMATION: Aptamer

<400> SEQUENCE: 5
cgcaatgggc g                                                              11

<210> SEQ ID NO 6
<211> LENGTH: 30
<212> TYPE: DNA
<213> ORGANISM: artificial
<220> FEATURE:
<223> OTHER INFORMATION: Aptamer

<400> SEQUENCE: 6
cgcaatgggc gcagattgga aggcctagca                                          30

<210> SEQ ID NO 7
<211> LENGTH: 24
<212> TYPE: DNA
<213> ORGANISM: artificial
<220> FEATURE:
<223> OTHER INFORMATION: P5 primer

<400> SEQUENCE: 7
gcctgttgtg agcctcctgt cgaa                                                24

<210> SEQ ID NO 8
<211> LENGTH: 23
<212> TYPE: DNA
<213> ORGANISM: artificial
<220> FEATURE:
<223> OTHER INFORMATION: Aptamer

<400> SEQUENCE: 8
ttgagcgttt attcttgtct ccc                                                 23

<210> SEQ ID NO 9
<211> LENGTH: 23
<212> TYPE: DNA
<213> ORGANISM: artificial
<220> FEATURE:
<223> OTHER INFORMATION: P3 primer

<400> SEQUENCE: 9
gggagacaag aataaacgct caa                                                 23
```

<210> SEQ ID NO 10
<211> LENGTH: 40
<212> TYPE: DNA
<213> ORGANISM: artificial
<220> FEATURE:
<223> OTHER INFORMATION: Aptamer

<400> SEQUENCE: 10
tcgaacgcaa tgggcgcaga ttggaaggcc tagcattgag                              40

<210> SEQ ID NO 11
<211> LENGTH: 36
<212> TYPE: DNA
<213> ORGANISM: artificial
<220> FEATURE:
<223> OTHER INFORMATION: Aptamer

<400> SEQUENCE: 11
gtcgaacgca atgggcgcag attggaaggc ctagca                                  36

<210> SEQ ID NO 12
<211> LENGTH: 22
<212> TYPE: DNA
<213> ORGANISM: artificial
<220> FEATURE:
<223> OTHER INFORMATION: Aptamer
<220> FEATURE:
<221> NAME/KEY: stem_loop
<222> LOCATION: (1)..(22)
<223> OTHER INFORMATION: stem between nucleotides 1 to 3 and 20 to 22
      loop between nucleotides 4 to 6 and 18 to 19 stem between
      nucleotides 7 to 9 and 15 to 17 loop between nucleotides 10 to 14
<220> FEATURE:
<221> NAME/KEY: misc_feature
<222> LOCATION: (1)..(22)
<223> OTHER INFORMATION: n is a, c, g, or t

<400> SEQUENCE: 12
nnnnnnnnnn nnnnnnnnnn nn                                                 22

<210> SEQ ID NO 13
<211> LENGTH: 43
<212> TYPE: DNA
<213> ORGANISM: artificial
<220> FEATURE:
<223> OTHER INFORMATION: Oligonucleotide
<220> FEATURE:
<221> NAME/KEY: misc_binding
<222> LOCATION: (20)..(21)
<223> OTHER INFORMATION: 6C3 between nucleotide 20 and nucleotide 21

<400> SEQUENCE: 13
actgactgac tgactgacta gggagacaag aataaacgct caa                          43

<210> SEQ ID NO 14
<211> LENGTH: 13
<212> TYPE: DNA
<213> ORGANISM: Artificial Sequence
<220> FEATURE:
<223> OTHER INFORMATION: P5 primer

<400> SEQUENCE: 14
gcctcctgtc gaa                                                           13

<210> SEQ ID NO 15
<211> LENGTH: 77
<212> TYPE: DNA

<213> ORGANISM: artificial
<220> FEATURE:
<223> OTHER INFORMATION: T10.1 aptamer
<220> FEATURE:
<221> NAME/KEY: stem_loop
<222> LOCATION: (1)..(77)
<223> OTHER INFORMATION: Loop from nucleotides 1 to 11 and 49 to 77, nucleotides 21 to 24 and 36 to 37, nucleotides 28 to 32, nucleotides 54 to 58. Stem from nucleotides 12 to 21 and 38 to 48, nucleotides 25 to 27 and 33 to 35, nucleotides 52 to 53 and 59 to 60

<400> SEQUENCE: 15
gcctgttgtg agcctcctgt cgaacgcaat gggcgcagat tggaaggcct agcattgagc    60
gtttattctt gtctccc    77

<210> SEQ ID NO 16
<211> LENGTH: 37
<212> TYPE: DNA
<213> ORGANISM: artificial
<220> FEATURE:
<223> OTHER INFORMATION: T10.1A aptamer
<220> FEATURE:
<221> NAME/KEY: stem_loop
<222> LOCATION: (1)..(37)
<223> OTHER INFORMATION: Stem from nucleotides 1 to 10 and 27 to 37, nucleotides 14 to 16 and 22 to 24. Loop from nucleotides 11 to 13 and 25 to 26, nucleotides 17 to 21

<400> SEQUENCE: 16
gcctcctgtc gaacgcaatg ggcgcagatt ggaaggc    37

<210> SEQ ID NO 17
<211> LENGTH: 30
<212> TYPE: DNA
<213> ORGANISM: artificial
<220> FEATURE:
<223> OTHER INFORMATION: T10.1B aptamer
<220> FEATURE:
<221> NAME/KEY: stem_loop
<222> LOCATION: (1)..(30)
<223> OTHER INFORMATION: Stem from nucleotides 1 to 7 and 24 to 30, nucleotides 11 to 13 and 19 to 21. Loop from nucleotides 8 to 10 and 22 to 23, nucleotides 14 to 18.

<400> SEQUENCE: 17
ccctgtcgaa cgcaatgggc gcagattggg    30

<210> SEQ ID NO 18
<211> LENGTH: 22
<212> TYPE: DNA
<213> ORGANISM: artificial
<220> FEATURE:
<223> OTHER INFORMATION: T10.1C aptamer
<220> FEATURE:
<221> NAME/KEY: stem_loop
<222> LOCATION: (1)..(22)
<223> OTHER INFORMATION: Stem from nucleotides 1 to 3 and 20 to 22, nucleotides 7 to 9 and 15 to 17. Loop from nucleotides 4 to 6 and 18 to 19, nucleotides 10 to 14

<400> SEQUENCE: 18
cccgaacgca atgggcgcag gg    22

<210> SEQ ID NO 19
<211> LENGTH: 11
<212> TYPE: DNA
<213> ORGANISM: artificial
<220> FEATURE:
<223> OTHER INFORMATION: T10.1D

```
<220> FEATURE:
<221> NAME/KEY: stem_loop
<222> LOCATION: (1)..(11)
<223> OTHER INFORMATION: Stem from nucleotides 1 to 3 and 9 to 11. Loop
      from nucleotides 4 to 8

<400> SEQUENCE: 19
cgcaatgggc g                                                              11
```

APTAMERS INHIBITING THE ENZYMATIC ACTIVITY OF TYROSINASE

CROSS REFERENCE TO RELATED APPLICATIONS

This application is a U.S. National Phase Application of PCT International Application Number PCT/EP2013/077801, filed on Dec. 20, 2013, designating the United States of America and published in the English language, which is an International Application of and claims the benefit of priority to French Patent Application No. 1262754, filed on Dec. 24, 2012. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is SeqList-REGI004-001APC.txt, the date of creation of the ASCII text file is Jun. 22, 2015, and the size of the ASCII text file is 3 KB.

The invention relates to the field of depigmenting or lightening dermocosmetic and dermatological applications.

In humans, pigmentation results from the synthesis and distribution of melanin pigments in the skin, hair follicles or eyes. Pigmentation is genetically predefined. Genes controlling pigmentation act directly on pigment cells, or indirectly on the environment of pigment cells, in particular keratinocytes.

Numerous genes acting on pigment cells have been identified and characterized, the products of which are proteins that control the synthesis of melanins, melanosome structural proteins, or that control melanosome biogenesis and transport.

Among exogenous factors that stimulate melanogenesis, ultraviolet rays rank first. Inflammation and oxidative stresses, such as those triggered by pollution, for example, stimulate melanin synthesis. These stresses act directly on melanocytes and also indirectly by activating keratinocytes which then release factors such as cytokines or hormones. These factors, such as interleukins, α-MSH, endothelin 1 and prostaglandins E2, trigger the sequence of reactions leading to melanin synthesis. These repeated stimulations, associated with disorders of the dermal-epidermal junction, cause the formation of heterogeneous skin pigmentation appearing, for example, as freckles, melasmas or lentigines.

Caused by excess of melanin in the skin, hyperpigmentations result from intrinsic factors (such as endocrine, metabolic or genetic factors) or extrinsic factors (such as photosensitizing, physical, chemical or inflammatory agents, etc.) which are sometimes closely linked and difficult to specify. Most hyperpigmentations result from melanocyte overactivity leading to melanin overproduction. These hyperpigmentations occur on the face or hands and appear as darker or more deeply colored areas or spots giving the skin a heterogeneous pigmentation.

All melanin pigments come from a common synthesis pathway involving an amino acid, tyrosine, and a key enzyme, tyrosinase, which may be free or in the form of a tyrosinase/tyrosine-related protein-1 complex. Tyrosinase transforms tyrosine into DOPA, then into DOPAquinone. From DOPAquinone two pathways are possible, one leading to pheomelanin, the other to eumelanin. In the eumelanin pathway, dopaquinone leads to the formation of dopachrome. The dopachrome via the formation of dihydroxyindole or dihydroxyindolecarboxyl leads to the formation of eumelanin. Tyrosinase is the key enzyme in this reaction sequence leading to the formation of melanin by catalyzing, alone or in a complex with tyrosinase-related protein 1, several reactions of this sequence.

Thus, in order to prevent hyperpigmentations and to inhibit melanogenesis, it is important to inhibit or eliminate tyrosinase activity in the skin.

Melanocytes express tyrosinase. Thus, it has been envisaged to develop specific tyrosinase inhibitors.

Natural or synthetic chemical compounds that regulate skin pigmentation can act via several types of mechanisms:
  by blocking the stimulation of melanocytes by keratinocytes, or
  by blocking the melanin synthesis pathway at a given point, or
  by blocking the transfer of melanosomes, or
  by decreasing the number of melanocytes.

Among these mechanisms of action, depigmenting agents can be inhibitors of the enzymatic activity of tyrosinase.

The first active agents used to regulate skin pigmentation and inhibit the enzymatic activity of tyrosinase were mercury salts, mercuric chloride, mercury amine chloride. Mercury competes with copper to inhibit tyrosinase activity, suppressing the first two phases of melanin synthesis. However, mercury is a highly toxic substance. Hydroquinone, hydroquinone ethers or derivatives have been proposed. It acts by competitive inhibition of tyrosinase. However, it induces mitochondrial changes and side effects such as irritations or allergies. Toxicology studies of these substances have shown a risk of skin cancer and inhibition of spermatogenesis.

The topical use of effective, harmless depigmenting substances is highly sought after in the fields of cosmetics and dermatology. These substances are used in particular to treat regional hyperpigmentations due to melanocyte hyperactivity such as idiopathic melasmas, localized hyperpigmentations due to melanocyte hyperactivity such as pigmentation spots known as solar lentigines and senile lentigines, accidental hyperpigmentations such as photosensitization or post-lesion healing, but also for leukodermas such as vitiligo. In the case of the latter, absent the ability to repigment the skin, pigmentation of the periphery of depigmented areas is attenuated to give the skin a more homogeneous color.

Depigmenting substances are also used as skin bleaching agents—in particular those indicated above, which are highly reactive to UV rays—to lighten the complexion, in particular the face and hands, in order to preserve the lightest possible skin color or to reduce the pigmenting effects of UV rays.

The aim of the invention is to solve the above-mentioned problems of the techniques of the prior art and to provide a cosmetic composition that is particularly advantageous for inhibiting the enzymatic activity of tyrosinase.

SUMMARY OF THE INVENTION

The invention relates to a novel topically-effective tyrosinase inhibitor for inhibiting melanogenesis which is stable in a cosmetically acceptable non-irritating, nontoxic and/or nonallergenic medium.

The invention also relates to a novel depigmenting agent acting on the melanogenesis process which is intended, on one hand, in the case of a substantially homogeneous pigmentation, for bleaching the skin, head hair or body hair, i.e., for decreasing their pigmentation, and, on the other hand, for preventing skin hyperpigmentation, namely when the pigmentation of the skin is heterogeneous.

Surprisingly, the inventors observed that a nuclease-resistant DNA aptamer that is capable of specifically binding to tyrosinase and inhibiting tyrosinase activity met all these criteria. In particular, it can penetrate skin cells.

To isolate anti-tyrosinase aptamers, the Inventors used a sequence library of phosphodiester oligonucleotide sequences (same composition as natural DNA). The selection was carried out in a directed manner to identify, isolate and characterize sequences that can specifically interact with tyrosinase.

These aptamers were then tested for their ability to inhibit tyrosinase activity.

A first object of the invention thus relates to a DNA aptamer, preferably resistant to nucleases, capable of inhibiting the enzymatic activity of tyrosinase and conversion of tyrosine into L-DOPA and Dopaquinone.

A second object of the invention relates to the use of an aptamer according to the invention to inhibit the enzymatic activity of tyrosinase.

A third object of the invention relates to a cosmetic or pharmaceutical composition comprising as active agent an aptamer according to the invention in an amount sufficient to inhibit tyrosinase and one or more pharmaceutically acceptable excipients.

A fourth object of the invention relates to the cosmetic use of an aptamer according to the invention.

A fifth object of the invention relates to an aptamer according to the invention as medication.

A sixth object of the invention relates to a method for selecting an aptamer according to the invention comprising the following steps:
Selecting in a DNA library, by means of the SELEX method, aptamers against the catalytic site of tyrosinase,
evaluating the potential to inhibit the enzymatic activity of tyrosinase of the aptamers identified in the preceding step,
cloning and sequencing the aptamers thus selected.

DETAILED DESCRIPTION OF THE INVENTION

A first object of the invention thus relates to a DNA aptamer, preferentially resistant to nucleases, that is capable of inhibiting the enzymatic activity of the tyrosinase protein which converts tyrosine into L-DOPA.

By "aptamer", it is meant a ligand-specific DNA or RNA molecule with high affinity for a protein. Consequently, this meaning comprises "natural" aptamers and chemically-modified analogs.

Aptamers are selected by the alternation of selection/amplification, which enables to direct the evolution of the population in a Darwinian manner: in the population, the most "apt" molecules are selected, hence the origin of the name "aptamers" given to oligonucleotides having the desired feature, stemming from the selection. Standard genetic engineering techniques (cloning, sequencing, expression) make it easy to identify these aptamers individually, then to characterize them and produce them in large amounts.

Aptamers can be selected by means of an optimized in vitro selection protocol known as systemic evolution of ligands by exponential enrichment (SELEX) (WO 91/19813).

The SELEX method enables to generate in large amounts ligands of very high affinity and specificity. This approach relies on the exposure of the target molecule to a library of potential ligands. A system of desorption/selection cycles enables to enrich the population of ligands that most specifically interact with the target molecule. The final population obtained is then isolated and characterized, allowing its large-scale resynthesis.

Although the SELEX method has been established as a general technique for selecting aptamers, it is neither predictive nor standardized for any target. On the contrary, the SELEX method must be optimized and adapted for each particular target. The SELEX method is not guaranteed for every target.

Several factors are important when selecting aptamers. For example, the target molecule must be stable and easily reproducible in each SELEX cycle, because the SELEX method involves several cycles of binding, selection and amplification. Additionally, nucleic acids that exhibit specific binding to the target must be present in the initial library. Thus, it is necessary to produce a highly-diversified initial nucleic acid library.

Selecting aptamers by means of the SELEX method is unpredictable. Even if all the factors are optimum for selecting aptamers, the SELEX method does not always enables the obtention of viable aptamers for each target.

The initial candidate library is composed of chemically synthesized DNA sequences, each comprising a long variable region of n nucleotides flanked, at the 3' and 5' ends, by identical constant regions for all the candidates of the library. These constant regions allow the central portion to be manipulated during SELEX, in particular by means of PCR. The length of the variable portion determines the library's diversity, which is equal to $4^n$ since each position can be occupied by one of four nucleotides A, T, G or C. For large windows, huge complexities arise: when n=50 theoretical diversity is $4^{50}$ ($10^{30}$), which is in practice an inaccessible value as it corresponds to more than $10^5$ tons for a library wherein each sequence is represented once. The experimental limit is around $10^{15}$ different sequences, which is that of a library wherein all candidates having a 25-nucleotide variable region are represented. If one chooses to manipulate a library comprising a 30-nucleotide window whose theoretical diversity is about $10^{18}$, only 1/1000 of the possibilities will thus be explored. In practice, that is generally sufficient to obtain aptamers having the desired properties. Additionally, since the polymerases used are unreliable and introduce errors at a rate on the order of $10^{-4}$, they contribute to significantly enrich the diversity of the sequence pool throughout the SELEX process: one candidate in 100 will be modified in each amplification cycle for a library with a random region of 100 nucleotides in length, thus leading to the appearance of $10^{13}$ new candidates for the overall library.

Selection in each round occurs by means of physical separation of molecules associated with the target from free molecules. Multiple techniques may be applied (chromatography, filter retention, electrophoresis, etc.). The selection conditions are adjusted (relative concentration of target/candidates, ion concentration, temperature, washing, etc.) so that a target-binding competition occurs between the candidates. Generally, stringency is increased as the rounds proceed in order to promote the capture of candidates with the highest affinity. In addition, counter-selection is carried out to eliminate candidates that recognize the support (filter, beads, etc.)

Oligonucleotides are oligo-anions, each unit having a charge at neutral pH, hydrogen-bond donor/acceptor sites, and an aromatic heterocycle (the nucleic base) that can generate stacking interactions. Following the formation of base pairs, these oligomers fold to generate secondary and tertiary structures. The initial sequence library is thus a library of three-dimensional shapes, each corresponding to a distribution of units that can trigger electrostatic interactions, create H bonds, etc. Selection becomes a question of identifying in the library the shape suited to the target, i.e., the shape allowing the greatest number of interactions and the formation of the most stable aptamer-target complex. For small targets (dyes, antibiotics, etc.) the aptamers identified are characterized by equilibrium dissociation constants in the micromolar range, whereas for protein targets $K_d$ values below $10^{-9}$ M are not rare.

Highly varied targets were aimed at in order to generate aptamers: amino acids, peptides, proteins and enzymes, and also complex structures such as intact viruses and living cells.

The most remarkable property of aptamers is the specificity of the interactions engaged with their ligand, making them ideal agents for target recognition.

Aptamers can be oligodeoxynucleotides (DNA) or oligoribonucleotides (RNA). In the latter case, the first SELEX step consists in transcribing the initial DNA library via the promoter sequence of the candidates 5' constant region. After selection, the candidates are converted into DNA by reverse transcription before being amplified. RNA and DNA aptamers having comparable characteristics were selected against the same target. Additionally, both compounds are competitive inhibitors of one another, suggesting overlapping interaction sites. That has major consequences for the production of chemically modified aptamers.

Development of the antisense approach led to synthesis of a large number of analogs, including some, for example, which give the oligomer resistance to nucleases, a property useful in a biological environment (cell culture medium or in vivo). Modifications of the phosphodiester bond, sugar or sugar-phosphate backbone, such as 2'-O-methyl, "locked" nucleic acid or boranophosphate derivatives, lead to nuclease-resistant oligomers. This property may be advantageous for aptamers. However, as mentioned above, the subsequent complete change of chemical structure of an aptamer selected in RNA or DNA form generally leads to a decrease in or a loss of the properties for which it was selected. That does not mean that it is not possible to introduce modifications at certain positions. But it is advisable to identify the positions at which modifications are tolerated. That can be carried out by testing specific variants or by a systematic approach, so-called chemical interference, which is a variant of footprinting.

It is of course preferable to directly perform the selection of non-natural oligonucleotides. That assumes that the modified nucleoside triphosphates are efficiently incorporated and the modified matrices are read correctly by the polymerases used during SELEX. A very small number of analogs meet the requirements. As for derivatives conferring resistance to nucleases, the possibilities are limited to phosphorothioate, boranophosphate or 2'-methyl-, 2'-amino- or 2'-fluoro-pyrimidine analogs, the latter being by far the most commonly used. The aptamers identified in this case have modified pyrimidine nucleosides and unmodified purine residues (2'-hydroxyl). These molecules have greater resistance to nucleases. If necessary, modified purine residues can be introduced later, as indicated above. Furthermore, it is possible to select oligonucleotides comprising substituents at the C(5) position of pyrimidines or the N(7), C(8) position of purines. That has no effect on sensitivity to nucleases, but makes it possible to add new functionalities (hydrophobicity, photoreactivity, etc.).

A very different approach relates to the use of optical isomers. Natural nucleic acids are D-isomers. L-analogs are resistant to nucleases but cannot be produced by polymerases. According to the laws of optical isomerism, an L-series aptamer will form with its target (T) a complex having the same characteristics as the complex formed by the D-series isomer and the enantiomer (T') of the target (T). Consequently, if compound T' can be chemically synthesized, it will be used to perform the selection of a natural aptamer (D). Once identified, this aptamer will be chemically synthesized in an L-series. This L-aptamer will be a ligand of the natural target (T).

Another approach, recently described as two-dimensional SELEX, simultaneously applies in vitro oligonucleotide selection and dynamic combinatorial chemistry (DCC), i.e., a reversible reaction between certain groups of the oligonucleotide (amine groups) and a library of aldehyde compounds. The reaction produces imine oligonucleotides which are selected on the same principles as for conventional SELEX. It was thus possible to identify for a target hairpin RNA modified aptamers that differ from natural aptamers.

Unlike backbone modifications which can alter the structure and which require precautions to be taken before being introduced in order to avoid losing aptamer-target interaction properties, it is possible to conjugate various groups at one of the 3' or 5 ends of the oligonucleotide in order to convert it into a tool, probe or sensor without disrupting its characteristics. This versatility constitutes in addition a significant advantage of aptamers, in particular in terms of diagnostics.

The expression "aptamer analog" means herein one or more modifications described above.

Preferably, the aptamer according to the invention can bind with high affinity to tyrosinase.

By "high affinity" is meant, in the context of the present invention, a specific interaction of the aptamer with the target and a dissociation constant that is sufficiently low to allow significant inhibition of the catalytic activity of the enzyme.

Preferably, the aptamer according to the invention comprises at least the sequence SEQ ID NO:5.

More preferentially, the aptamer according to the invention comprises at least one sequence selected from the group consisting of SEQ ID NO:1, SEQ ID NO:2, SEQ ID NO:3, SEQ ID NO:4 and SEQ ID NO:6.

The sequence SEQ ID NO:1 has been selected by the SELEX method.

The sequences SEQ ID NO:2 to 5 are shortened derivatives of SEQ ID NO:1.

The sequence SEQ ID NO:6 corresponds to the portion of SEQ ID NO:1 without the primers.

Table 1 below summarizes these sequences.

TABLE 1

Sequences of shortened DNA aptamers stemming from aptamer T10.1 representing 42% of round 10.

| | | |
|---|---|---|
| T10.1<br>SEQ ID<br>NO: 1 | GCCTGTTGTGAGCCTCCTGTCGAACGCAATGGGCGCAGATTGGAAGGCCTAGCATTGAGCGTTTATTCTTGTCTCCC<br>⎵_______⎵ ⎵__________________⎵ ⎵_______________⎵ ⎵____________________⎵<br>　　　SEQ ID NO: 7　　　　SEQ ID NO: 6　　　　SEQ ID NO: 8 | SEQ ID<br>NO: 1 |
| T10.1A<br>SEQ ID<br>NO: 2 | GCCTCCTGTCGAACGCAATGGGCGCAGATTGGAAGGC | SEQ ID<br>NO: 2 |
| T10.1B<br>SEQ ID<br>NO: 3 | CCTGTCGAACGCAATGGGCGCAGATTGGG | SEQ ID<br>NO: 3 |
| T10.1C<br>SEQ ID<br>NO: 4 | CCCGAACGCAATGGGCGCAGGG | SEQ ID<br>NO: 4 |
| T10.1D<br>SEQ ID<br>NO: 5 | CGCAATGGGCG | SEQ ID<br>NO: 5 |

More preferentially, the aptamer according to the invention comprises at least 10 contiguous nucleotides of SEQ ID NO:6 flanked in 5' by one or more contiguous nucleotides of the sequence SEQ ID NO:7 starting from its 3' end and/or flanked in 3' by one or more contiguous nucleotides of the sequence SEQ ID NO:8 starting from its 5' end.

More preferentially, the aptamer according to the invention comprises SEQ ID NO:6 flanked in 3' by one or more contiguous nucleotides of the sequence SEQ ID NO:7 starting from its 5' end and/or flanked in 5' by one or more contiguous nucleotides of the sequence SEQ ID NO:8 starting from its 3' end.

By "one or more", it is meant any number of nucleotides, preferably 3 to 10, in a particularly preferred manner 5 nucleotides.

For example, mention may be made of the sequences:

SEQ ID NO:10: TCGAACGCAATGGGCGCAGATTG-GAAGGCCTAGCATTGAG comprising SEQ ID NO:6 flanked in 5' by 5 contiguous nucleotides of the 3' end of SEQ ID NO:7 and flanked in 3' by 5 contiguous nucleotides of the 5' end of SEQ ID NO:8, SEQ ID NO:11: GTCGAACGCAATGGGCGCAGAT-TGGAAGGCCTAGCA comprising SEQ ID NO:6 flanked in 5' by 6 contiguous nucleotides of the 3' end of SEQ ID NO:7.

The aptamer according to the invention may also comprise a sequence derived from T10.1C (SEQ ID NO:4 or SEQ ID NO:18) of the same apical stem-loop-stem-loop secondary structure (see FIG. 1), each stem consisting of G-C, C-G, A-T or T-A pairs, each loop comprising 2 to 10 nucleotides.

This sequence may also be expressed as follows:
$X_1$ - - - $X_n X_{(n+1)}$ - - - $X_m X_{(m+1)}$ - - - $X_p X_{(p+1)}$ - - - $X_r$
$X_{(r+1)}$ - - - $X_o X_{(o+1)}$ - - - $X_s X_{(s+1)}$ - - - $X_t$
wherein each X is a nucleotide
$1 \leq n \leq 5$
$n+1 \leq m \leq n+5$, preferably $n+1 \leq m \leq n+3$
$m+1 \leq p \leq m+5$
$p+1 \leq r \leq p+10$, preferably $p+2 \leq r \leq p+8$, in a particularly preferred manner $r=p+5$
$r+1 \leq o \leq r+5$
$o+1 \leq s \leq o+5$
$s+1 \leq t \leq s+5$
$t-s=n$
$o-r=p-m$
n, m, p, r, o, s, t are integers and signify the position of the nucleotide,
nucleotides $X_1$ to $X_n$ and $X_{(s+1)}$ to $X_t$ are A, T, G or C, preferably G or C, provided that they are paired and thus form a stem,
nucleotides $X_{(m+1)}$ to $X_p$ and $X_{(r+1)}$ to $X_o$ are A, T, G or C, preferably G or C, provided that they are paired and thus form a stem,
nucleotides $X_{(n+1)}$ to $X_m$ and $X_{(o+1)}$ to $X_s$ are A, T, G or C and are unpaired and thus form a loop,
nucleotides $X_{(p+1)}$ to $X_r$ are A, T, G or C and are unpaired and thus form a loop.

A "stem" is a perfectly paired double-stranded sequence, for example:
G-C A-T
C-G A-T
G-C A-T
C-G A-T A "loop" is an unpaired motif within a double-stranded sequence.

According to a particular embodiment of the invention, the aptamer according to the invention comprises a sequence derived from T10.1C (SEQ ID NO:4 or SEQ ID NO:18) of the same apical stem-loop-stem-loop secondary structure (see FIG. 1), each stem consisting of three G-C, C-G, A-T or T-A pairs, each loop comprising 5 nucleotides.

This sequence SEQ ID NO:12 may also be expressed as follows:
$X_1$ - - - $X_n X_{(n+1)}$ - - - $X_m X_{(m+1)}$ - - - $X_p X_{(p+1)}$ - - - $X_r$
$X_{(r+1)}$ - - - $X_o X_{(o+1)}$ - - - $X_s X_{(s+1)}$ - - - $X_t$
wherein each X is a nucleotide
n=3
m=n+3
p=m+3
r=p+5
o=r+3
s=o+2
t=s+3
n, m, p, r, o, s, t are integers and signify the position of the nucleotide,
nucleotides $X_1$ to $X_n$ and $X_{(s+1)}$ to $X_t$ are A, T, G or C, preferably G or C, provided that they are paired and thus form a stem, nucleotides $X_{(m+1)}$ to $X_p$ and $X_{(r+1)}$ to $X_o$ are A, T, G or C, preferably G or C, provided that they are paired and thus form a stem, nucleotides $X_{(n+1)}$ to $X_m$ and $X_{(o+1)}$ to $X_s$ are A, T, G or C and are unpaired and thus form a loop, nucleotides $X_{(p+1)}$ to $X_r$ are A, T, G or C and are unpaired and thus form a loop.

A "stem" is a perfectly paired double-stranded sequence, for example:

G-C A-T
C-G A-T
G-C A-T
C-G A-T

Another object of the invention relate to the use of an aptamer according to the invention to inhibit the enzymatic activity of tyrosinase.

Tyrosinase transforms tyrosine into L-DOPA. The enzymatic activity of tyrosinase can be evaluated by measuring the appearance of DOPAchrome, a colored oxidation product of L-DOPA. The kinetics of appearance of this oxidation product is monitored by measuring absorbance at 450 nm.

Preferably, the invention relates to the use of an aptamer according to the invention as a skin depigmenting or lightening agent in a cosmetic or dermatological composition.

Another object of the invention relates to a cosmetic or pharmaceutical composition comprising as active agent at least one aptamer according to the invention in an amount sufficient to inhibit the enzyme activity of tyrosinase and one or more cosmetically/pharmaceutically acceptable excipients.

Preferably, the composition of the invention comprises from 0.00001% to 10%, preferably from 0.00005% to 5%, more preferably from 0.001% to 1% of one or more aptamers according to the invention. Generally, any composition of the invention may be applied to the skin or skin appendages.

It may be provided in all pharmaceutical forms suitable for topical application.

The composition of the invention may in particular have the form of aqueous or oily solutions or of lotion- or serum-type dispersions, milk-type emulsions with a liquid or semi-liquid consistency, obtained by dispersion of an aqueous phase in a silicone phase (H/Si), of a fatty phase in an aqueous phase (oil-in-water emulsion) or, conversely, of an aqueous phase in a fatty phase (water-in-oil emulsion), or aqueous or anhydrous suspensions or emulsions with a cream- or gel-type soft consistency, or of microcapsules or microparticles, or of ionic and/or nonionic-type vesicular dispersions, or of foams. These compositions are prepared using conventional methods. The amounts of the various components of the compositions according to the invention are those typically used in the fields under consideration.

In the field of cosmetics, these compositions constitute in particular creams for cleansing, protecting, treating or caring for the face, hands, feet or body (for example, day creams, night creams, makeup remover creams, foundation creams, sunscreen creams), liquid foundations, makeup remover milks, body protection or care milks, sunscreen milks, skincare lotions, gels or foams, such as cleansing lotions, sunscreen lotions, artificial tanning lotions, compositions for the bath, deodorant compositions comprising a bactericide, aftershave gels or lotions, depilatory creams.

The compositions according to the invention may also consist of powder or non-powder solid preparations, for example in the form of a stick, a compacted powder, cleansing soaps or bars. It may be provided also as patches, pencils, brushes and applicators allowing localized application on spots on the face or hands. It may be used as a care product or as a makeup product.

When the composition is an emulsion, the proportion of fatty phase may vary from about 5% to 80% by weight, and preferably from about 5% to 50% by weight in relation to the total weight of the composition. The oils, waxes, emulsifiers and co-emulsifiers used in the composition in emulsion form are selected from those typically used in the field of cosmetics. The emulsifier and co-emulsifier are present in the composition in a proportion of 0.3% to 30% by weight, and preferably of 0.5% to 20% by weight in relation to the total weight of the composition. In addition, the emulsion may contain lipid vesicles.

When the composition is an oily solution or gel, the fatty phase may represent more than 90% of the total weight of the composition.

In a known manner, the cosmetic or pharmaceutical composition of the invention may also contain adjuvants commonly used in the field of cosmetics or pharmaceuticals, such as hydrophilic or lipophilic gelling agents, hydrophilic or lipophilic active agents, preservatives, antioxidants, solvents, fragrances, fillers, filters, pigments, odor absorbers and colorants. The amounts of these various adjuvants are those typically used in the fields under consideration. These adjuvants, according to their nature, may be added to the fatty phase, to the aqueous phase, to lipid vesicles or to nanoparticles. The amounts of these various adjuvants are those typically used in the field of cosmetics or pharmaceuticals and vary, for example, from about 0.01% to 10% of the total weight of the composition. These adjuvants, according to their nature, may be added to the fatty phase, to the aqueous phase and/or to lipid spherules.

Exemplary oils or waxes which may be employed in the invention include mineral oils (liquid paraffin), plant oils (liquid fraction of shea butter, sunflower oil), animal oils (perhydrosqualene), synthetic oils (Purcellin oil), silicone oils or waxes (cyclomethicone) and fluoro oils (perfluoropolyethers), beeswax, carnauba wax or paraffin wax. To these oils fatty alcohols and fatty acids (stearic acid) may be added. Exemplary emulsifiers which may be employed in the invention include, for example, glycerol stearate, polysorbate 60 and the mixture PEG-6/PEG-32/Glycol Stearate sold under the name Tefose 63 by the company Gattefossé.

Exemplary solvents which may be employed in the invention include the lower alcohols, in particular ethanol and isopropanol, and propylene glycol.

Exemplary hydrophilic gelling agents which may be employed in the invention include carboxyvinyl polymers (carbomers), acrylic copolymers such as acrylate/alkylacrylate copolymers, polyacrylamides, polysaccharides such as hydroxypropylcellulose, natural gums and clays, and exemplary lipophilic gelling agents include modified clays such as bentones, metal salts of fatty acids such as aluminum stearates, hydrophobic silica, ethylcellulose and polyethylene.

A composition of the invention may also comprise one or more additional active agents, for example intended to inhibit melanogenesis.

The aforesaid active agents which may be employed in combination with the aptamers according to the invention, used pure or from extracts containing these molecules, are in particular the following compounds: ellagic acid and derivatives thereof; hydroquinone; arbutin; resorcinol and derivatives thereof; vitamin C and derivatives thereof; pantothenate sulfonate and derivatives thereof; kojic acid; molecules that interfere directly or indirectly with alpha-melanocyte stimulating hormone (α-MSH) or its receptor or adrenocorticotropic hormone (ACTH); polyols such as glycerin, glycol or propylene glycol; vitamins; keratolytic agents or desquamative agents such as salicylic acid and derivatives thereof; alpha-hydroxy acids such as lactic acid or malic acid, alone or grafted; beta-hydroxy acids; ascorbic acid and derivatives thereof; retinoic acid; retinaldehyde; retinol and derivatives thereof such as palmitate, propionate or acetate, in a liposomal preparation or not; antiglycation agents or antioxidants, taken alone or in combination, such as tocopherol and derivatives thereof, thiotaurine, hypotaurine, aminoguanidine, thiamine pyrophosphate, pyridoxamine, lysine, histidine, arginine, phenylalanine, pyridoxine, adenosine triphosphate; anti-inflammatory agents such as stearyl glycyrrhetinate; soothing agents and mixtures thereof, chemical or physical sunscreens such as octyl methoxycinnamate, butyl-methoxydibenzoylmethane, micronized titanium oxide and zinc oxide; and deoxyribonucleic or nucleic acids.

The present invention also concerns the use of at least one aptamer according to the invention for the manufacture of a medication intended to be administered simultaneously, separately or sequentially in combination with one or more other active agents, for example the active agents described above.

The present invention also has as an object the use of at least one aptamer according to the invention in a cosmetic or dermatological composition for depigmenting or lightening human skin, head hair or body hair, or to remove or attenuate pigmentation spots on human skin.

The present invention also has as an object the use of at least one aptamer according to the invention in or for the manufacture of a cosmetic or dermatological composition as inhibitor of the synthesis of melanins.

The present invention also concerns the use of at least one aptamer according to the invention to modulate the expression of tyrosinase.

The present invention also has as an object the use of at least one aptamer according to the invention in a cosmetic composition that depigments or lightens human skin.

The present invention also has as an object the use of at least one aptamer according to the invention for the manufacture of a dermatological composition that depigments or lightens human skin.

Another object of the invention relates to the cosmetic use of an aptamer according to the invention, preferably for depigmenting or lightening the skin, body hair and/or head hair.

The present invention also relates to a method of cosmetic or dermatological treatment to control excess pigmentation, to depigment or to lighten human skin consisting in applying on the skin a cosmetic or dermatological composition comprising at least one aptamer according to the invention.

The present invention also relates to the use of at least one aptamer according to the invention for the manufacture of a medication intended for the topical treatment or prevention of diseases resulting in overexpression of tyrosinase.

Another object of the invention concerns an aptamer according to the invention for use in the treatment or prevention of hyperpigmentations such as regional hyperpigmentations due to melanocyte hyperactivity such as idiopathic melasmas, localized hyperpigmentations due to benign melanocyte hyperactivity and proliferation such as age or liver spots (senile lentigines), accidental hyperpigmentations such as photosensitization or hyperpigmentation related to scarring, and for the treatment of certain leukodermas such as vitiligo.

Another object of the invention relates to an aptamer according to the invention as medication, preferably intended to lighten or depigment the skin, body hair and/or head hair.

Another object of the invention relates to an aptamer according to the invention for use in the treatment or prevention of hyperpigmentations such as regional hyperpigmentations due to melanocyte hyperactivity such as idiopathic melasmas, localized hyperpigmentations due to benign melanocyte hyperactivity and proliferation such as age or liver spots (senile lentigines), accidental hyperpigmentations such as photosensitization or hyperpigmentation related to scarring, and for the treatment of certain leukodermas such as vitiligo.

The aptamers according to the invention may be used according to the invention in vectorized form, i.e., linked to a vector. This type of vector is well-known to the person skilled in the art. For example, it may be a cholesterol residue or nanoparticles.

The aptamers according to the invention may also be used according to the invention in the form of dimers of two aptamers or a conjugate of several aptamers.

Another object of the invention relates to a method for selecting an aptamer according to the invention comprising the following steps:
  Selecting in a DNA library, by means of the SELEX method, aptamers against tyrosinase,
  evaluating the potential to inhibit the enzymatic activity of tyrosinase of the aptamers identified in the preceding step,
  cloning and sequencing the aptamer thus selected.

Example 1: Materials and Methods for Selecting Anti-Tyrosinase Aptamers

Proteins

Recombinant human tyrosinase (TYR) protein containing an N-terminal GST tag was provided by Abnova. The polyhistidine-GST tag was produced at the European Institute of Chemistry and Biology.

Oligonucleotides and Libraries

A DNA library and primers provided by Sigma were purified by HPLC. The primer sequences (P3) 5' GGGAGACAAGAATAAACGCTCAA (SEQ ID NO:9) and (P5) 5' GCCTGTTGTGAGCCTCCTGTCGAA (SEQ ID NO:7) were used for amplification of the library containing a randomly selected 30-nucleotide window. The sequence 5' ACTGACTGACTGACTGACTA-6C3-GGGAGA-CAAGAATAAACGCTCAA (SEQ ID NO:13) was used to produce the single strand as described in the literature (Williams K P, Bartel D P. *PCR product with strands of unequal length. Nucleic Acids Res.* 1995 Oct. 25; 23(20): 4220-1). The 5' biotinylated primer (P3) was used to produce single-stranded candidate DNAs. The candidate DNAs were synthesized and purified by HPLC by Eurogentec (Table 1). Before every experiment the DNA populations and candidates were heated at 75° C. for 5 minutes, placed on ice for 5 minutes, and then placed at room temperature for at least 5 minutes.

In Vitro Selection

Before selection the DNA library (1 nanomole) was treated as described above and incubated with filters (0.45 μm HAWP, Millipore) twice for the first and second rounds and once for all other rounds in PBS—Mg buffer (154 mM NaCl, 1 mM $KH_2PO_4$, 2.96 mM $Na_2HPO_4.7H_2O$, 1 mM $(CH_3COO)_2Mg$) for 20 minutes at room temperature. In each round, an additional counter-selection was carried out against the polyhistidine-GST tag. Next, the counter-selected library was mixed with tyrosinase (20 picomoles) for 20 minutes and the unbound candidates were separated by means of the filter retention technique. After filtering, the candidates bound to tyrosinase were eluted by incubation for 20 minutes at 65° C. in 500 µl of 7 M phenol/urea, precipitated and amplified by PCR to produce the single strand used for the following round of selection. Reducing the amount of candidates and target during selection to reach 25 and 1 picomoles, respectively, in the tenth round increased the stringency of the selection. Before cloning, the populations of each round of selection were evaluated for their ability to inhibit tyrosinase activity.

Cloning and Sequencing

The sequences selected from rounds 7 and 10 were cloned using the TOPO TA Cloning Kit (Invitrogen) and were sequenced using the BigDye Terminator v1.1 Cycle Sequencing Kit (Applied Biosystems) according to the manufacturers' instructions.

Characterization of Surface Plasmon Resonance (SPR) Candidates

All the experiments were carried out on a Biacore 3000 device with PBS—Mg buffer at 23° C. The biotinylated oligonucleotides—heated at 75° C. for 5 minutes, placed on ice for 5 minutes and then placed at room temperature for at least 5 minutes—were immobilized on streptavidin-coated sensor chips (XanTec bioanalytics). The oligonucleotides were injected at 100 nM for 4 minutes at 5 µl/min to reach 800 to 1000 RU.

Tyrosinase and the GST-His control were injected at 500 nM and 1 µM at a rate of 20 µl/min at 23° C. The same injections were carried out with PBS—Mg buffer and tyrosinase storage buffer to subtract the effects of the buffer from the specific sensorgram.

After each injection of proteins, the functionalized surface of the sensor chip was regenerated with a mixture of 40% formamide, 3.6 M urea and 30 mM EDTA for a 1-minute pulse.

The data were analyzed using the BIA eval 4.1 software.

Example 2: Results of the Selection of Anti-Tyrosinase Aptamers

The procedure of selection-amplification against the target, tyrosinase, was repeated 10 times; SELEX rounds 7 and 10 were cloned and sequenced. Forty-one and 74 candidate DNAs from rounds 7 and 10, respectively, were analyzed. Sequence T10.1 represents 42% of the sequences of round 10. The other sequences show great diversity. Sequence T10.1 was not present in round 7.

Figure 1:
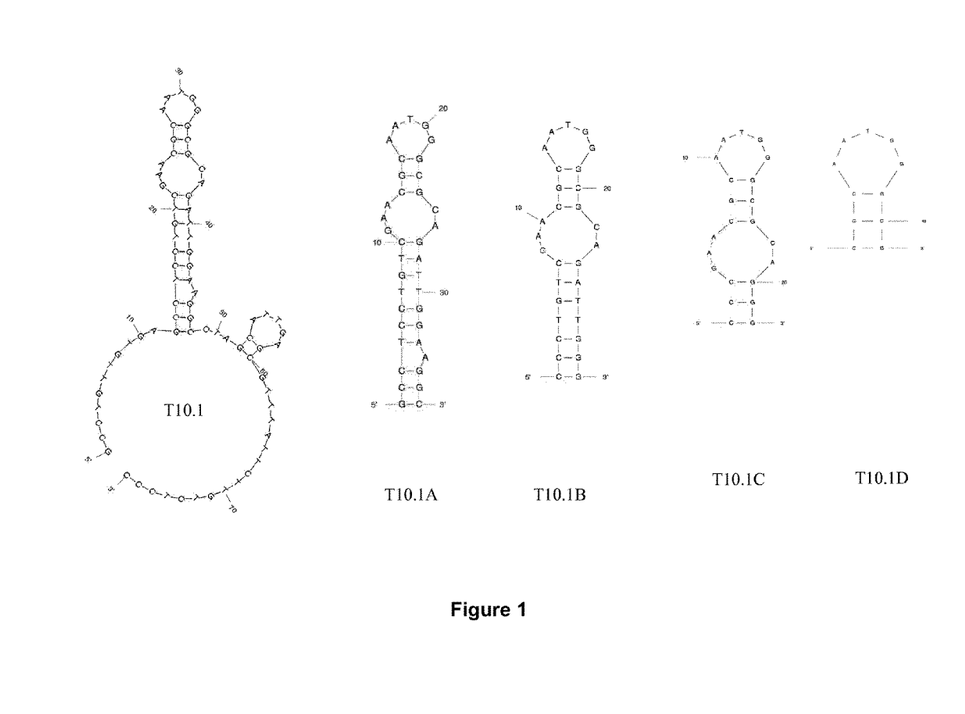
FIG. 1: Predicted secondary structures of aptamer T10.1 and truncated versions thereof.

The secondary structure of candidate T10.1 (SEQ ID NO: 15) was predicted using the mfold software (Zuker, M., 2003. Nucleic Acids Res 31(13), 3406-3415). A long imperfect stem-loop including part of 5' primer P5 (GCCTCCT-GTCGAA; SEQ ID NO:14) and showing a potential 5-nucleotide internal loop and a 5-nucleotide apical loop was predicted (FIG. 1).

Figure 2:
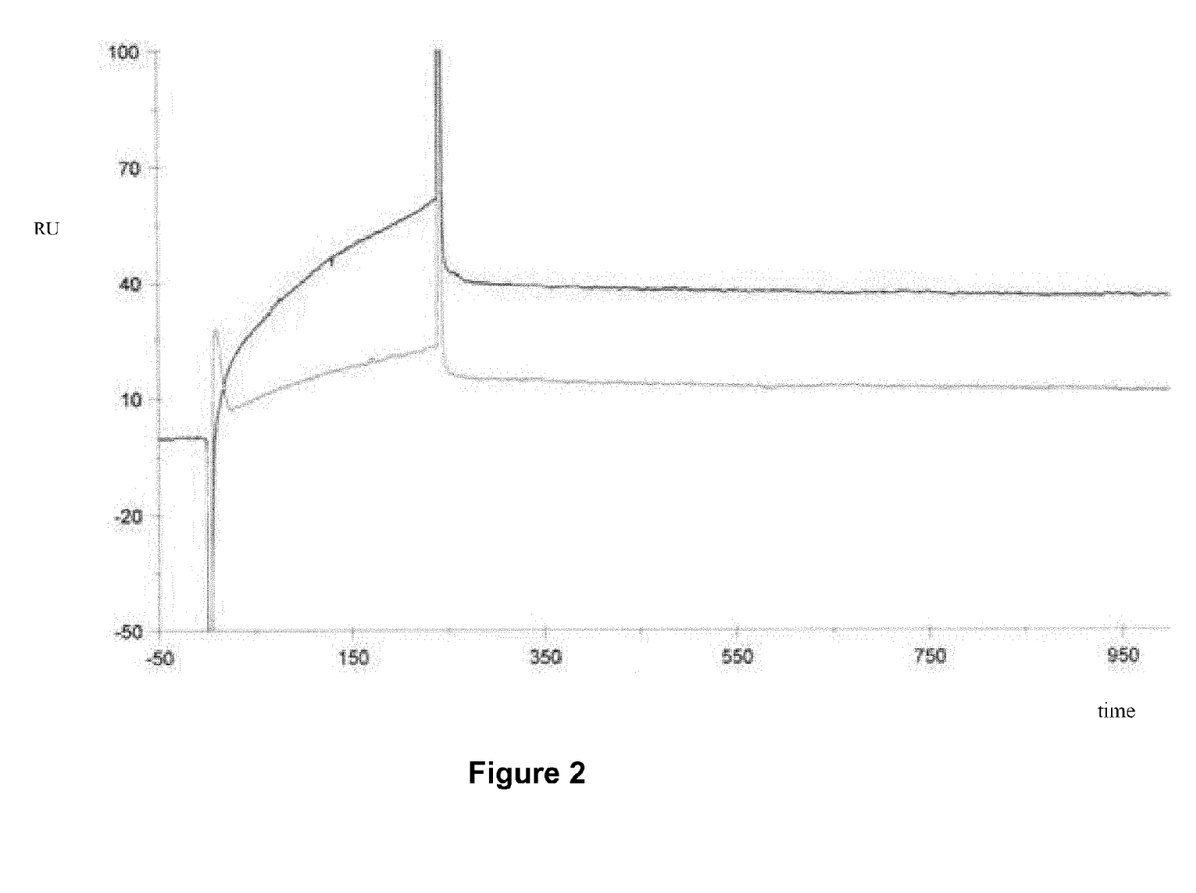
FIG. 2: Sensorgram of the aptamer T10.1-tyrosinase complex

The binding of this candidate, T10.1, and of truncated versions derived from the full-length candidate (Table 1) was investigated by surface plasmon resonance (SPR). About 1000 resonance units (RU) of biotinylated candidate T10.1 were immobilized and tyrosinase was injected at 500 nM or 1 µM. Signals of 16 and 42 RU were detected for 500 nM and 1 µM, respectively, indicating interaction between candidate T10.1 and tyrosinase (FIG. 2).

Example 3: Measuring Tyrosinase Activity 3.1 Principle

An enzyme is a protein that can specifically catalyze the transformation of one or two substrates. Taking a simplified enzymatic reaction model:

reaction rate is written:

$$v = \frac{d(P)}{dt} = -\frac{d(S)}{dt}.$$

To plot a (P)=f (t) curve, the enzyme (E) acts on the substrate (S); time zero corresponds to triggering of the reaction. Appearance of the product (P) is measured as a function of time (see FIG. 4).

Figure 4:
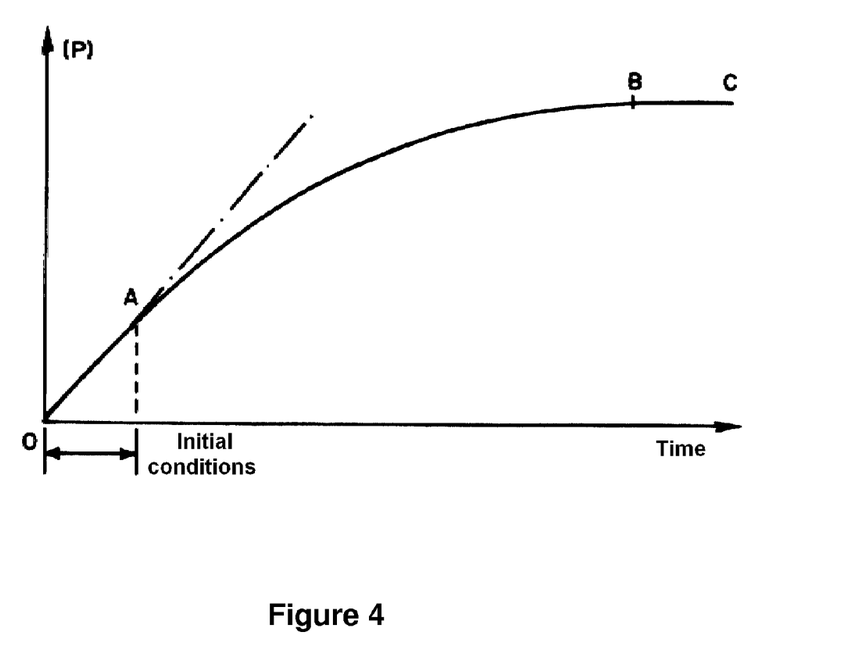
FIG. 4: (P)=f(t) curve, relationship between the appearance of the product (P) and time (t).

The reaction rate $$v = \frac{d(P)}{dt}$$

is constant during the initial conditions (0 A portion of the curve). For this portion of the curve, the tangent through the origin merges with the curve: the rate, which is the slope of tangent 0 A, is called the initial rate. The rate then decreases (AB portion of the curve) and becomes zero (BC portion). The rate becomes zero when one of the substrates is consumed or when equilibrium is established.

When the rate of an enzymatic reaction is determined, it is always the initial rate that is calculated. Rate measurements are thus made under the initial conditions wherein less than 10% of the amount of substrate is hydrolyzed. While $[S] \gg [E]$, the initial rate is proportional to enzyme concentration: it thus reflects the activity of an enzyme preparation expressed in enzyme units.

The enzymatic activity of tyrosinase is measured by detecting the colored oxidation product of tyrosinase's product. Tyrosinase's product, L-DOPA, is oxidized into a colored product, dopachrome. The kinetics of appearance of this product of successive oxidation of L-DOPA and then of L-dopaquinone is monitored by measuring absorbance at 450 nm.

3.2 Measuring the Enzymatic Activity of Tyrosinase in a Melanocyte Culture

Normal human melanocytes are seeded in 96-well microplates at a concentration of $1 \times 10^4$ cells per well. After 72 hours of treatment with the various candidates from round 10 and candidates stemming from round 10 (T10.1 (SEQ ID NO: 15), T.10.1A (SEQ ID NO:16), T10.1B (SEQ ID NO:17), T10.1C (SEQ ID NO:18), T10.1D (SEQ ID NO:19)), the enzymatic activity of tyrosinase is determined. Each aptamer is tested at four increasing concentrations: 4, 20, 100 and 200 nM.

The cells are rinsed with PBS, then 50 µl of Triton X100 (0.5%) is added to each well and the plate is shaken for one hour at 4° C. The reaction is triggered by adding 50 µl of substrate (10 mM L-DOPA, Sigma) to each well. The appearance of dopachrome is measured every 2 minutes at 450 nm for 1 hour and at 37° C., with steady shaking. The reaction rates thus obtained are expressed in OD units/ minute.

Variations in absorbance (450 nm) over time are monitored using a BMG POLARstar plate reader spectrophotometer at +20° C. The curve representing absorbance (in absorbance units) as a function of time (in minutes) is plotted.

The initial rate of the reaction is determined by calculating the slope of the tangent through the origin. $V_0$ represents the initial rate in the absence of effector and $V_i$ represents this rate in the presence of an effector. The ratio $(V_i/V_0) \times 100$ is calculated: if this ratio equals 100, the effector has no effect on the activity of the enzyme; if it is below 100, the effector is an inhibitor of the activity of the enzyme; if it is above 100, it is an activator. The results of this measurement are presented in FIG. 3.

Figure 3:
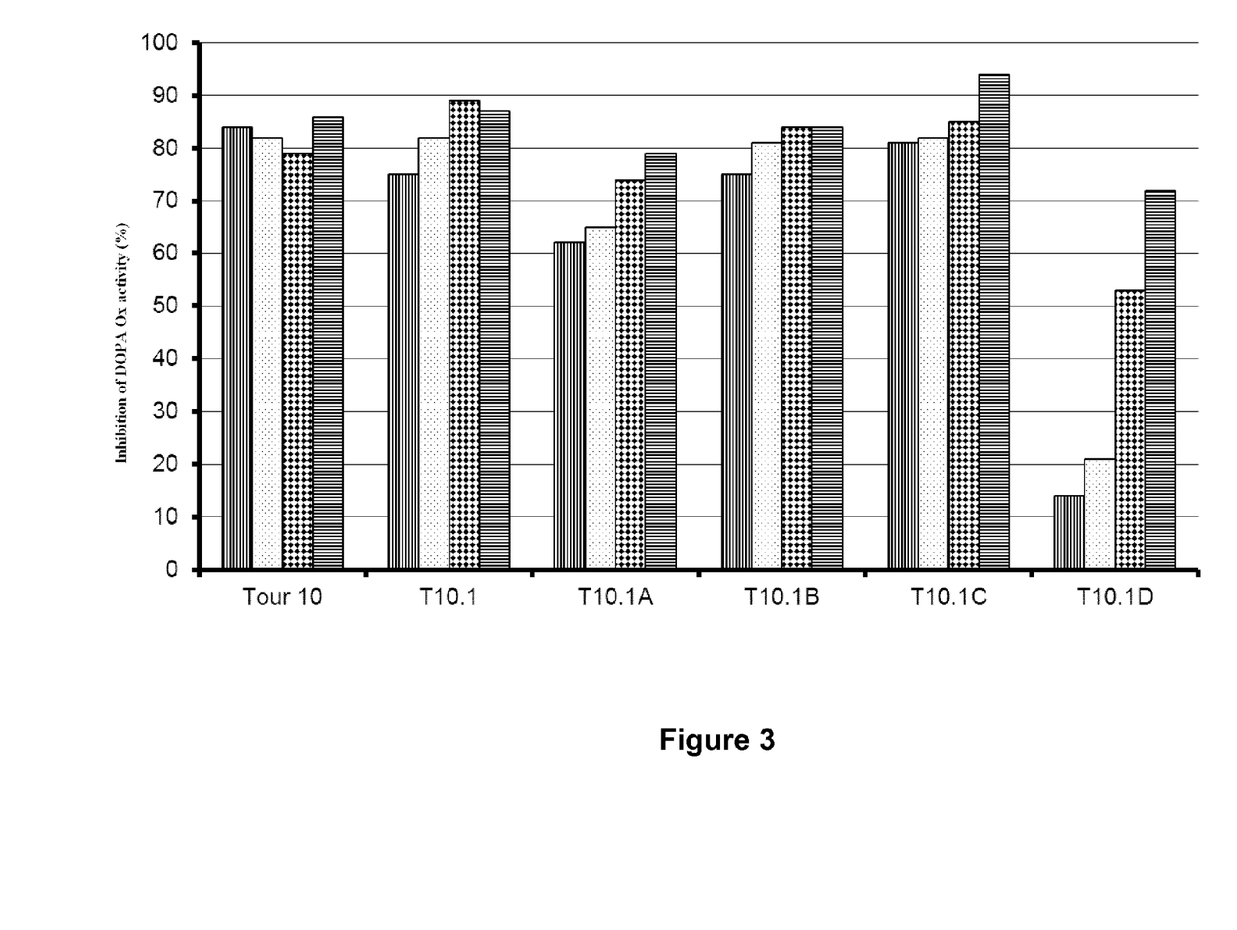
FIG. 3: Measurement of modulation of tyrosinase activity by various aptamers from round 10.

The results presented in FIG. 3 show that each candidate tested has an inhibitory effect on tyrosinase activity. This effect is significant for each condition tested, except at the lowest concentrations of the most shortened candidate, T10.1D (4 and 20 nM).

The set of candidates constituting round 10 have a significant effect—greater than 75%—on tyrosinase activity whatever the concentration tested. No dose-dependent effect is observed. Similar results are obtained for the T10.1 candidates.

Shortened candidates T10.1A and T10.1B are both also inhibitors of tyrosinase activity. However, this inhibition is inferior to that of the full-size round 10 candidate and of T10.1, in particular at the lowest concentrations (4 and 20 nM).

Candidate T10.1C has a very good ability to inhibit this enzyme regardless of the concentration tested. In particular, a nearly 95% inhibition of tyrosinase activity is noted for this candidate when used at a concentration of 200 nM. No other candidate tested at this concentration has activity this high.

The most shortened candidate, T10.1D, has the lowest inhibitory activity regardless of the concentration tested.

These results suggest the absence in the structure of aptamer T10.1D of a region important to tyrosinase inhibition activity.

Exemplary Formulations

Example A: Cosmetic Powder for Lightening the Complexion of the Face

| | |
|---|---|
| Microcellulose | 20.00% |
| Sodium lauryl sulfoacetate | 15.00% |
| Aptamer according to the invention | 1% |
| Fragrance, colorants, preservatives | qs |
| Talc | qs to 100% |

This powder has a dual action. It cleanses the skin and, moreover, by regular use for several days, lightens the complexion. It can be applied to the skin of the face twice a day.

Example B: Cosmetic Depigmenting Day Cream in Emulsion-Gel Form

| | |
|---|---|
| Glycerin | 5.00% |
| Caprylic/capric/succinic triglycerides | 5.00% |
| Octyl methoxycinnamate | 1.00% |
| Dimethicone copolyol | 0.50% |
| Acrylates/C10-30 alkyl acrylate crosspolymer | 0.50% |
| Aptamer according to the invention | 1% |
| Neutralizer | qs |
| Preservatives, fragrance, colorants | qs |
| Water | qs to 100% |

Some people exposed to relatively intense daylight radiation, or even direct sunlight, wish to maintain a light complexion and to avoid the appearance of pigmented spots. Use of the emulsion-gel above will make it possible to achieve this aim. This composition is generally applied to the face in the morning. It acts both to prevent and to treat pigmentation, uniform or not, of the face.

Example C: Cosmetic Liquid Sunscreen Composition (SPF 30)

| | |
|---|---|
| Volatile pentacyclomethicone | 49.00% |
| Titanium dioxide | 15.00% |
| Octyl methoxycinnamate | 7.50% |
| Glycerin | 5.00% |
| Phenyltrimethicone | 5.00% |
| Dimethicone copolyol | 3.00% |
| Polymethylmethacrylate | 2.50% |
| Butyl methoxydibenzoyle methane | 1.00% |
| Aptamer according to the invention | 1% |
| Neutralizer, fragrance, preservatives, antioxidants | qs |
| Water | qs to 100% |

This composition is to be used before exposure to intense sunlight. It prevents the appearance of pigmentation spots in people predisposed to this phenomenon. It should be noted that the presence of a high concentration of sunscreen compensates for reduced natural protection, a consequence of a decrease in the level of melanin.

Example D: Dermatological Cream for Treating Skin Hyperpigmentations Caused by Pathology or Trauma

| | |
|---|---|
| Glyceryl stearate + Peg-100 stearate | 5.00% |
| Hydrogenated polyisobutene | 4.00% |
| Magnesium ascorbyl phosphate | 3.00% |
| Tricaprylate/glycerol caprate | 3.00% |
| Squalane | 3.00% |
| Glycerin | 2.00% |
| Beeswax | 1.50% |
| Cetearyl octanoate | 1.50% |
| Cetyl alcohol | 1.00% |
| Stearyl alcohol | 1.00% |
| Dimethicone | 1.00% |
| Xanthan gum | 0.30% |
| Ethylenediaminetetraacetic acid | 0.20% |
| Citric acid | 0.10% |
| Sodium citrate | 0.10% |
| Aptamer according to the invention | 1% |
| Neutralizer, fragrance, preservatives | qs |
| Water | qs to 100% |

Use of this cream attenuates skin hyperpigmentations caused by pathology or trauma. This cream also attenuates color contrasts at the periphery of depigmented areas in the case of vitiligo.

Example E: Cosmetic Face Lotion for Lightening the Complexion

| | |
|---|---|
| Ethyl alcohol | 30.00% |
| PPG-3 Myristyl ether | 5.00% |
| Glycerin | 2.00% |
| Carbomer | 0.20% |
| Polysorbate 20 | 0.20% |
| Aptamer according to the invention | 1% |
| Neutralizer, fragrance, preservatives | qs |
| Water | qs to 100% |

This lotion for lightening the complexion is used after removing makeup and cleansing the skin.

Example F: Cosmetic Lightening Serum for the Face

| | |
|---|---|
| Water | qs to 100% |
| Glycerin | 2% |
| Tetrasodium EDTA | qs to desired pH |
| Citric acid | |
| Trisodium citrate | |
| Xanthan gum | 0.25% |
| Polyacrylamide, C13.14 isoparaffin, laureth-7 | 0.5% |
| Dimethicone copolyol | 0.25% |
| Aptamer according to the invention | 1% |
| Fragrance, colorant, preservative | qs |

A drop of this highly concentrated serum composition is applied to the face generally before applying face cream. This serum is typically used in a one- or two-week treatment to obtain or maintain a lightened complexion.

Example G: Cosmetic Lotion for Lightening Body Hair

| | |
|---|---|
| Water | qs to 100% |
| Alcohol | 50% |
| Panthenylethyl ether | 0.5% |
| DL-α-Tocopherol acetate | 0.2% |
| Polysorbate 60 | 1% |
| Aptamer according to the invention | 1% |
| Fragrance | 0.2% |
| Glycerin | 0.5% |
| Colorant | qs |

This lotion is applied to the hairy areas to be lightened, in particular the arms, for a period sufficient to obtain progressive lightening of the hairs.

Example H: Spot-Preventing Cosmetic Cream Gel for the Hands

| | |
|---|---|
| Caprylic/capric diglyceryl succinate | 6% |
| Octyl octanoate | 2.5% |
| Octyl methoxycinnamate | 6% |
| Aptamer according to the invention | 1% |
| Phenyltrimethicone | 2.5% |
| Benzophenone-3 | 0.5% |
| Sodium hyaluronate | 0.05% |
| Xanthan gum | 0.2% |
| Acrylates/C10.30 alkyl acrylate copolymer | 0.5% |
| Glycerin | 2% |
| PEG 150 | 3% |
| Neutralizers, colorants, fragrance, preservatives | qs |
| Purified water | qs to 100% |

This cream should be applied directly to spots (solar and/or senile lentigines) on the hands in order to attenuate the color of the spots.

---

What is claimed is:

1. A DNA aptamer that inhibits the enzymatic activity of tyrosinase for the conversion of tyrosine into L-DOPA and dopaquinone, said aptamer comprising sequence SEQ ID NO:5.

2. The DNA aptamer according to claim 1, wherein said DNA aptamer binds with high affinity to tyrosinase.

3. The DNA aptamer according to claim 1, that is resistant to nucleases.

4. The DNA aptamer according to claim 1, comprising a sequence selected from the group consisting of SEQ ID NO:1, SEQ ID NO:2, SEQ ID NO:3, SEQ ID NO:4 and SEQ ID NO:6.

5. The DNA aptamer according to claim 1, comprising at least 10 contiguous nucleotides of SEQ ID NO:6 flanked in 5' by one or more contiguous nucleotides of the sequence SEQ ID NO:7 starting from its 3' end and/or flanked in 3' by one or more contiguous nucleotides of the sequence SEQ ID NO:8 starting from its 5' end.

6. The DNA aptamer according to claim 5, comprising SEQ ID NO:6 flanked in 5' by one or more contiguous nucleotides of the sequence SEQ ID NO:7 starting from its 3' end and/or flanked in 3' by one or more contiguous nucleotides of the sequence SEQ ID NO:8 starting from its 5' end.

7. The DNA aptamer according to claim 1, comprising the following sequence:

$X_1 - - - X_n X_{(n+1)} - - - X_m X_{(m+1)} - - - X_p X_{(p+1)} - - - X_r X_{(r+1)} - - - X_o X_{(o+1)} - - - X_s X_{(s+1)} - - - X_t$ wherein each X is a nucleotide $1 \leq n \leq 5$ $n+1 \leq m \leq n+5$ $m+1 \leq p \leq m+5$ $p+1 \leq r \leq p+10$, $p+2 \leq r \leq p+8$, or $r = p+5$ $r+1 \leq o \leq r+5$ $o+1 \leq s \leq o+5$ $s+1 \leq t \leq s+5$ $t-s = n$ $o-r = p-m$ n, m, p, r, o, s, t are integers and signify the position of the nucleotide, nucleotides $X_1$ to $X_n$ and $X_{(s+1)}$ to $X_t$ are A, T, G or C, provided that they are paired and thus form a stem, nucleotides $X_{(m+1)}$ to $X_p$ and $X_{(r+1)}$ to $X_o$ are A, T, G or C, provided that they are paired and thus form a stem, nucleotides $X_{(n+1)}$ to $X_m$ and $X_{(o+1)}$ to $X_s$ are A, T, G or C and are unpaired and thus form a loop, nucleotides $X_{(p+1)}$ to $X_r$ are A, T, G or C and are unpaired and thus form a loop.

8. A method of using at least one DNA aptamer according to claim 1, to inhibit the enzymatic activity of tyrosinase comprising contacting a tyrosinase with at least one aptamer according to claim 1.

9. A cosmetic or pharmaceutical composition comprising as an active agent a DNA aptamer according to claim 1 in an amount sufficient to inhibit the enzyme activity of tyrosinase and one or more cosmetically/pharmaceutically acceptable excipients.

10. The composition according to claim 9, wherein said composition comprises from 0.00001% to 10%, from 0.00005% to 5%, from 0.001% to 1% by weight of the composition, of one or more DNA aptamers.

11. A method of using the DNA aptamer according to claim 1, for depigmenting or lightening the skin, body hair and/or head hair comprising contacting the DNA aptamer of claim 1 with skin or hair of a subject.

12. The DNA aptamer according to claim 1, wherein said DNA aptamer is formulated in a medication.

13. A method of using the DNA aptamer of claim 1 to treat or prevent regional hyperpigmentations due to melanocyte hyperactivity such as idiopathic melasmas, localized hyperpigmentations due to benign melanocyte hyperactivity and proliferation, age or liver spots (senile lentigines), accidental hyperpigmentations, photosensitization or hyperpigmentation related to scarring, leukodermas, or vitiligo comprising contacting the DNA aptamer of claim 1 with the skin of a subject in need thereof.

14. A method for selecting a DNA aptamer according to claim 1 comprising:

selecting in a DNA library, by the SELEX method, DNA aptamers against tyrosinase, evaluating the potential to inhibit the enzymatic activity of tyrosinase of the DNA aptamers identified in the preceding step, and cloning and sequencing the DNA aptamers thus selected.

* * * * *

UNITED STATES PATENT AND TRADEMARK OFFICE
CERTIFICATE OF CORRECTION

PATENT NO. : 9,732,348 B2
APPLICATION NO. : 14/654950
DATED : August 15, 2017
INVENTOR(S) : Cauchard et al.

Page 1 of 1

It is certified that error appears in the above-identified patent and that said Letters Patent is hereby corrected as shown below:

On the Title Page

Item (73) Assignees:, change "L V M H Recherché," to --L V M H Recherche,--.

In the Specification

In Column 3 at Lines 46-47, after "complex" insert --.--.

In Column 16 at Line 29 (approx.), change "methoxydibenzoyle methane" to --methoxydibenzoylmethane--.

In the Claims

In Column 25 at Line 54 (approx.), in Claim 7, change "$X_{(s+1)}$ to $X_1$" to --$X_{(s+1)}$ to $X_r$--.

Signed and Sealed this
Twenty-eighth Day of May, 2019

Andrei Iancu
*Director of the United States Patent and Trademark Office*